US012697358B2

(12) United States Patent
Ho et al.

(10) Patent No.: US 12,697,358 B2
(45) Date of Patent: Aug. 4, 2026

(54) LACTIC ACID BACTERIAL COMPOSITION FOR MODULATING IMMUNE CELL DIFFERENTIATION AND/OR REDUCING PRO-INFLAMMATORY CYTOKINE SECRETION AND USE THEREOF

(71) Applicant: GLAC BIOTECH CO., LTD, Tainan (TW)

(72) Inventors: Hsieh-Hsun Ho, Tainan (TW); Shin-Yu Tsai, Tainan (TW); Yi-Wei Kuo, Tainan (TW); Jia-Hung Lin, Tainan (TW); Ko-Chiang Hsia, Tainan (TW); Yu-Hshan Chin, Tainan (TW)

(73) Assignee: GLAC BIOTECH CO., LTD., Tainan (TW)

( * ) Notice: Subject to any disclaimer, the term of this patent is extended or adjusted under 35 U.S.C. 154(b) by 199 days.

(21) Appl. No.: 18/429,790

(22) Filed: Feb. 1, 2024

(65) Prior Publication Data

US 2025/0041357 A1 Feb. 6, 2025

(30) Foreign Application Priority Data

Aug. 2, 2023 (TW) ................................. 112129148

(51) Int. Cl.
| | |
|---|---|
| *A61K 35/744* | (2015.01) |
| *A61K 35/00* | (2006.01) |
| *C12N 1/205* | (2026.01) |
| *C12R 1/01* | (2006.01) |

(52) U.S. Cl.
CPC ........... *A61K 35/744* (2013.01); *C12N 1/205* (2021.05); *A61K 2035/115* (2013.01); *C12R 2001/01* (2021.05)

(58) Field of Classification Search
CPC ............ A61K 35/744; A61K 2035/115; A61K 35/747; C12N 1/205; C12N 1/20; C12R 2001/01; C12R 2001/225; A61P 11/02; A61P 29/00
See application file for complete search history.

(56) References Cited

FOREIGN PATENT DOCUMENTS

CN 109512854 B * 9/2021

OTHER PUBLICATIONS

Steiner NC, Lorentz A. Probiotic Potential of Lactobacillus Species in Allergic Rhinitis. Int Arch Allergy Immunol. 2021; 182(9):807-818. doi: 10.1159/000515352. Epub Apr. 21, 2021. PMID: 33882482. (Year: 2021).*

* cited by examiner

*Primary Examiner* — Kade Ariani
(74) *Attorney, Agent, or Firm* — Troutman Pepper Locke LLP; Tim Tingkang Xia, Esq.

(57) ABSTRACT

A lactic acid bacterial composition for modulating immune cell differentiation and/or reducing pro-inflammatory cytokine secretion includes: (a) a *Limosilactobacillus reuteri* GL-104 strain; and (b) a *Lacticaseibacillus rhamnosus* F-1 strain; wherein the GL-104 strain is deposited at the China Center for Type Culture Collection with a deposition number CCTCC M209138, and the F-1 strain is deposited at the China Center for Type Culture Collection with a deposition number CCTCC M2011124. Additionally, a method for treating or preventing allergic rhinitis by administering the foregoing composition to a subject in need thereof is also provided.

5 Claims, 6 Drawing Sheets

LACTIC ACID BACTERIAL COMPOSITION FOR MODULATING IMMUNE CELL DIFFERENTIATION AND/OR REDUCING PRO-INFLAMMATORY CYTOKINE SECRETION AND USE THEREOF

CROSS REFERENCE

This non-provisional application claims priority of Taiwan Invention Patent Application No. 112129148, filed on Aug. 2, 2023, the contents thereof are incorporated by reference herein.

FIELD OF THE INVENTION

The present invention is involved in the art of probiotics, and more particularly to a lactic acid bacterial composition for modulating immune cell differentiation and/or reducing pro-inflammatory cytokine secretion and use of the foregoing composition, e.g., treating or preventing allergic rhinitis.

BACKGROUND OF THE INVENTION

Allergic rhinitis is a type of rhinitis caused by allergens in air affecting the immune system. Its main symptoms include: rhinorrhea, nasal congestion, excessive sneezing, eye itching, or tearing, and its common allergens comprise: pollen, dust mites, or pet dander. Although allergic rhinitis can't lead to life-threatening, it can significantly bring harmful effects to the quality of daily life, e.g., inability to concentrate, insomnia, dizziness, or fatigue.

The occurrence of allergic rhinitis is related to the immune cell differentiation. Monocytes can differentiate into macrophages, and macrophages can be divided into three phenotypes: M0 phenotype, M1 phenotype, and M2 phenotype. M0 macrophages can be polarized into M1 macrophages or M2 macrophages with the environmental condition. M1 macrophages have a receptor CD86 highly expressed on the cell surface, and M1 macrophages can induce inflammatory response, which can help fight off infection, increase T cell activity, and withstand or eliminate lesion tissues. M2 macrophages have a receptor CD206 highly expressed on the cell surface, and M2 macrophages are responsible for eliminating inflammatory response and tissue repair. In a patient suffering from allergic rhinitis, macrophages are preferentially polarized into M1 macrophages, which makes inflammatory response too strong to induce symptoms including rhinorrhea, nasal congestion, sneezing, and eye itching. When the M2 macrophage number decreases, the ability to inhibit allergy lowers, and consequently the allergic symptom becomes more serious.

CXCL10 (C-X-C motif chemokine 10) is also called as "interferon-7 inducible protein 10 kD (IP-10)", and it can recruit T cells and other leukocytes, e.g., natural killer cells or dendritic cells. The study indicates that the expression level of CXCL10 is increased in the nasal mucosa of a patient suffering from allergic rhinitis, and the expression level is proportional to the condition severity. In an animal model of allergic rhinitis, it is further found that inhibiting the CXCL10 expression can eliminate the symptoms of rhinitis.

Allergic response has a close relation to gut health. That is, the intestinal microflora composition has a direct correlation with the occurrence of an allergic disease. Generally, the higher the intestinal microflora diversity is, the better the health status is. The study demonstrates that probiotics can modulate the reaction of an immune system, maintain the tight conjunction between intestinal cells, inhibit harmful microorganisms, generate short-chain fatty acids, and lower the allergic response caused by leaky gut syndrome. The in vitro test demonstrates that probiotics can promote the polarization of macrophages to M2 phenotype to eliminate allergy and improve the symptoms of allergic rhinitis, which can provide a new perspective for developing the elimination of the related symptom.

Therefore, there is a need to develop a probiotic formulation for modulating an immune system, which is safe and suitable to be taken for a long period. It is well known that a probiotic product belongs to a food or a health supplement, and is an over-the-counter drug so it can't harmfully impact on a human body. Accordingly, an objective in the art is to provide a probiotic formulation for improving the immune-related disease.

SUMMARY OF THE INVENTION

The present invention is made based on the finding that a combination of specific lactic acid bacterial strains can reduce the production of pro-inflammatory cytokine CXCL10 by an immune cell and increase the ratio of CD206 to CD86 on the cell surface.

Therefore, an objective of the present invention is to provide a lactic acid bacterial composition for modulating immune cell differentiation and/or reducing pro-inflammatory cytokine secretion, the composition including: (a) a *Limosilactobacillus reuteri* GL-104 strain; and (b) a *Lacticaseibacillus rhamnosus* F-1 strain; wherein the GL-104 strain is deposited at the China Center for Type Culture Collection with a deposition number CCTCC M209138, and the F-1 strain is deposited at the China Center for Type Culture Collection with a deposition number CCTCC M2011124.

Exemplarily, relative to a total bacterial count of the GL-104 strain and the F-1 strain, the GL-104 strain is present at 10% to 90%, and the F-1 strain is present at 10% to 90%.

Exemplarily, relative to a total bacterial count of the GL-104 strain and the F-1 strain, the GL-104 strain is present at 10%, 20%, 30%, 40%, 50%, 60%, 70%, 80%, or 90%, and the F-1 strain is present at 10%, 20%, 30%, 40%, 50%, 60%, 70%, 80%, or 90%.

Exemplarily, relative to a total bacterial count of the GL-104 strain and the F-1 strain, the GL-104 strain is present at 30%, and the F-1 strain is present at 70%.

Exemplarily, the GL-104 strain is a viable strain or an inactivated strain, and the F-1 strain is a viable strain or an inactivated strain.

Exemplarily, the lactic acid bacterial composition further comprises: (c) an excipient, diluent, or carrier.

Exemplarily, the excipient, diluent, or carrier is a food-acceptable excipient, diluent, or carrier, or a pharmaceutical-acceptable excipient, diluent, or carrier.

Another objective of the present invention is to provide a method for treating or preventing allergic rhinitis, the method including: administering the foregoing composition to a subject in need thereof.

Exemplarily, the composition treats or prevents the allergic rhinitis through reducing production of pro-inflammatory cytokine CXCL10 by an immune cell.

Exemplarily, the composition treats or prevents the allergic rhinitis through increasing a ratio of CD206 to CD86 on a surface of an immune cell.

BRIEF DESCRIPTION OF THE DRAWINGS

The above and other objects, features and other advantages of the present invention and examples will be more clearly understood in conjunction with the accompanying drawings, in which.

DETAILED DESCRIPTION OF THE INVENTION

Figure 1:
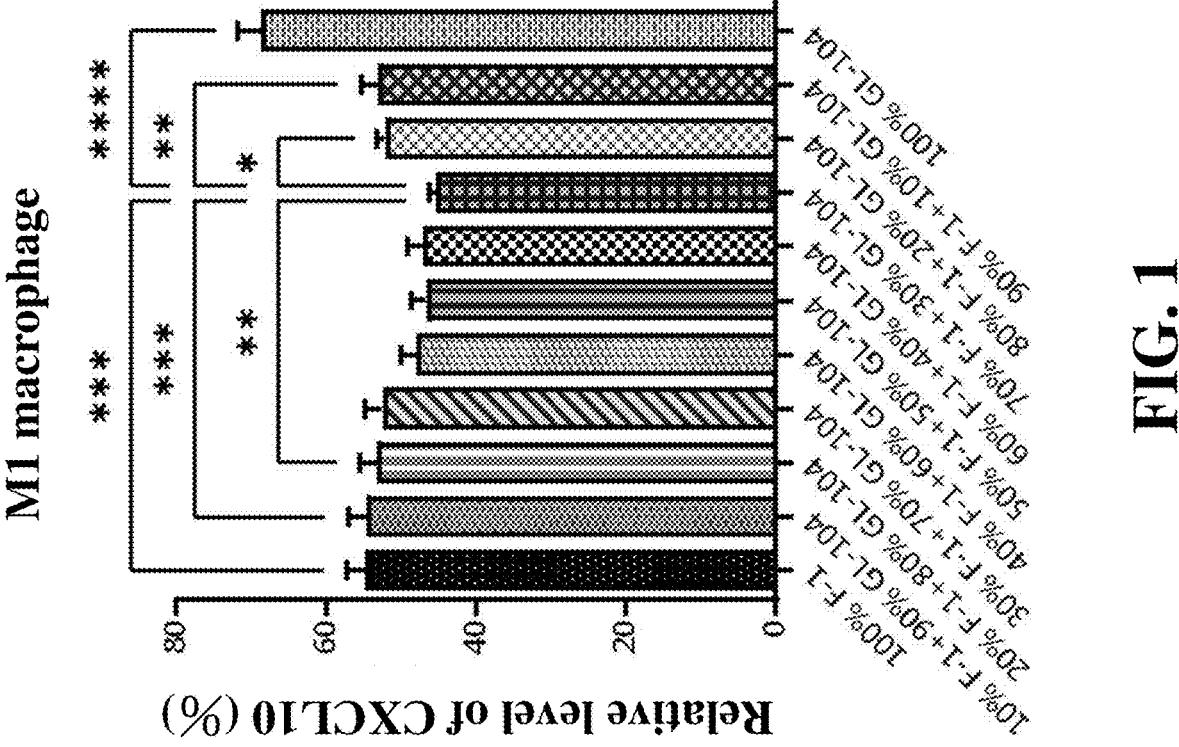
FIG. 1 is a bar graph illustrating the effect of mixing a GL-104 strain and a F-1 strain at different ratios on pro-inflammatory cytokine CXCL10 expression by M1 macrophages, wherein * indicates $P<0.05$,  indicates $P<0.01$, * indicates $P<0.001$, and **** indicates $P<0.0001$.

The detailed description and preferred embodiments of the invention will be set forth in the following content, and provided for people skilled in the art to understand the characteristics of the invention.

Lactic acid bacterial strains described herein are deposited at the China Center for Type Culture Collection in Wuhan University, Wuhan City, China in the form of freeze-dried culture. The deposition information is listed in Table 1 below.

TABLE 1

| deposition information | | | |
| --- | --- | --- | --- |
| Strain | Classification | Deposition number | Deposition date |
| GL-104 | *Limosilactobacillus reuteri* | CCTCC M209138 | Aug. 7, 2009 |
| F-1 | *Lacticaseibacillus rhamnosus* | CCTCC M2011124 | Apr. 10, 2011 |

It is found herein that a *Limosilactobacillus reuteri* GL-104 strain and a *Lacticaseibacillus rhamnosus* F-1 strain can cooperate in reducing pro-inflammatory cytokine CXCL10 secretion by macrophages and promoting polarization of macrophages to M2 phenotype. Therefore, the thus-obtained lactic acid bacterial combination can be used in treating or preventing allergic rhinitis.

According to an embodiment of the present invention, a lactic acid bacterial composition for modulating immune cell differentiation and/or reducing pro-inflammatory cytokine secretion is provided, and the composition includes: a *Limosilactobacillus reuteri* GL-104 strain, which is deposited at the China Center for Type Culture Collection with a deposition number CCTCC M209138, and a *Lacticaseibacillus rhamnosus* F-1 strain, which is deposited at the China Center for Type Culture Collection with a deposition number CCTCC M2011124.

The composition may further comprise: an excipient, diluent, or carrier for allowing the composition to be in various forms. The excipient, diluent, or carrier is, but not limited to a food-acceptable excipient, diluent, or carrier, or a pharmaceutical-acceptable excipient, diluent, or carrier.

On the condition that the excipient, diluent, or carrier is a food-acceptable excipient, diluent, or carrier, the composition is a food composition. The example of a food-acceptable excipient, diluent, or carrier is, but not limited to a food. The food may be, but not limited to a fluid milk (e.g., a milk or a condensed milk), a fermented milk (e.g., a soured milk), a milk powder, an ice cream, a cheese, a cottage cheese, a soy milk, a fermented soy milk, a vegetable juice, a fruit juice, a sports drink, a jelly, a cookie, an energy bar, a health food, an animal feed, or a dietary supplement.

On the condition that the excipient, diluent, or carrier is a pharmaceutical-acceptable excipient, diluent, or carrier, the composition is a pharmaceutical composition. The example of a pharmaceutical-acceptable excipient, diluent, or carrier is, but not limited to a solvent, a buffer agent, an emulsifying agent, a suspending agent, a decomposing agent, a disintegrant, a dispersant, a binder, a stabilizing agent, a chelating agent, a gelling agent, a humectant, a lubricant, an absorption delaying agent, or a liposome.

Additionally, based on a total bacterial count of the GL-104 strain and the F-1 strain, the GL-104 strain may be present at 10% to 90%, and the F-1 strain may be present at 10% to 90%; preferably, the GL-104 strain is present at 10%, 20%, 30%, 40%, 50%, 60%, 70%, 80%, or 90%, and the F-1 strain is present at 10%, 20%, 30%, 40%, 50%, 60%, 70%, 80%, or 90%; more preferably, the GL-104 strain is present at 30%, and the F-1 strain is present at 70%.

As described above, the composition can reduce the CXCL10 secretion by macrophages and promote the macrophage polarization to M2 phenotype, and therefore the composition can be used in treating or preventing the disease or the symptom caused by the CXCL10 hypersecretion by macrophages and the macrophage hyperpolarization to M1 phenotype, e.g., allergic rhinitis.

According to another embodiment of the present invention, a method for treating or preventing allergic rhinitis is provided, and the method comprises: administering the foregoing composition to a subject in need thereof. Specifically, the composition achieves the purpose of treating or preventing allergic rhinitis by reducing the production of pro-inflammatory cytokine CXCL10 by an immune cell (e.g., a macrophage) and increasing the ratio of CD206 to CD86 on the cell surface of an immune cell (e.g., a macrophage).

More specifically, the composition can be administered to a subject in need of treating or preventing allergic rhinitis so as to treat or prevent allergic rhinitis. The term "administering" used herein may comprise but not limited to, oral route, sublingual route, rectal route, intranasal route, vaginal route, intraperitoneal route, transdermal route, intraepidermal route, intraarticular route, intraocular route, or ocular surface route. The term "subject" used herein may be, but not limited to a mammal; the example of a mammal may be, but not limited to a primate, a cat, a dog, a mouse, a rat, a rabbit, a cow, a horse, a goat, a sheep, or a pig; the examples of a primate may be, but not limited to a chimpanzee, a human, a gorilla, a bonobo, an orangutan, or a monkey.

On the condition that the subject is a human, the administration may be, but not limited to at a total bacterial count of the GL-104 strain and the F-1 strain from $10^6$ to $10^{10}$ CFU/kg of body weight of the subject per day; preferably, the administration is at a total bacterial count of the GL-104 strain and the F-1 strain from $10^7$ to $10^9$ CFU/kg of body weight of the subject per day; more preferably, the administration is at a total bacterial count of the GL-104 strain and the F-1 strain of 108 CFU/kg of body weight of the subject per day.

The following examples are offered for further illustrating the invention.

Example 1: Morphological and Common Property of Bacterial Strain

The 16S ribosomal RNA (rRNA) sequencing and the API bacterial identification system are used to identify taxonomy properties of bacterial strains. Morphological properties and common properties of bacterial strains are listed in Table 2 below.

TABLE 2 morphological and common property of bacterial strain

| Strain | Property |
|---|---|
| *Limosilactobacillus reuteri* GL-104 strain | 1. They are Gram-positive bacteria. They are non-sporogenous bacteria without catalase and oxidase and without mobility. They can survive both in an aerobic environment or in an anaerobic environment, and the suitable growth temperature is 37 ± 1° C.; they are facultative heterofermentative bacteria and can't produce any gas during glucose metabolism. 2. They grow on a MRS agar medium in the form of a solid white circle. The bacterial bodies are in the form of a short rod, and two ends thereof are in the form of a circle; they usually appear alone. |
| *Lacticaseibacillus rhamnosus* F-1 strain | 1. They are Gram-positive bacteria. They are non-sporogenous bacteria without catalase and oxidase and without mobility. They can survive both in an aerobic environment or in an anaerobic environment, and the suitable growth temperature is 37 ± 1° C.; they are facultative heterofermentative bacteria and can't produce any gas during glucose metabolism. 2. They grow on a MRS agar medium in the form of a solid white circle. The bacterial bodies are in the form of a short rod, and two ends thereof are in the form of a square; they usually appear alone. |

Example 2: Production of Bacterial Solution

A bacterial strain is stocked in a glycerol solution (20%) at −80° C. After being taken from the environment of −80° C., the bacterial strain is activated at 37° C. for 24 hours with an MRS broth medium containing 0.05% cysteine. After which, the bacterial strain is pelleted and suspended with an appropriate amount of phosphate buffered saline (PBS), and then its concentration is adjusted to $10^9$ CFU/mL.

The composition and the bacterial count of each probiotic sample obtained by mixing different bacterial solutions are listed in Table 3.

TABLE 3 composition and bacterial count of probiotic sample

| | Bacterial count of GL-104 (CFU) | Bacterial count of F-1 (CFU) |
|---|---|---|
| 100% F-1 | — | $8 \times 10^6$ |
| 10% F-1 + 90% GL-104 | $7.2 \times 10^6$ | $8 \times 10^5$ |
| 20% F-1 + 80% GL-104 | $6.4 \times 10^6$ | $1.6 \times 10^6$ |
| 30% F-1 + 70% GL-104 | $5.6 \times 10^6$ | $2.4 \times 10^6$ |
| 40% F-1 + 60% GL-104 | $4.8 \times 10^6$ | $3.2 \times 10^6$ |
| 50% F-1 + 50% GL-104 | $4.0 \times 10^6$ | $4.0 \times 10^6$ |
| 60% F-1 + 40% GL-104 | $3.2 \times 10^6$ | $4.8 \times 10^6$ |
| 70% F-1 + 30% GL-104 | $2.4 \times 10^6$ | $5.6 \times 10^6$ |
| 80% F-1 + 20% GL-104 | $1.6 \times 10^6$ | $6.4 \times 10^6$ |
| 90% F-1 + 10% GL-104 | $8 \times 10^5$ | $7.2 \times 10^6$ |
| 100% GL-104 | $8 \times 10^6$ | — |

The carbon source used in the bacterial culture medium of the present example may be glucose, fructose, lactose, sucrose, maltose, galactose, mannose, trehalose, starch, molasses, potato starch, corn starch, malt extract, maltodextrin, or any combination thereof. For example, the used culture medium includes a 2 wt % to 5 wt % mixture containing glucose and maltodextrin; preferably, the liquid culture medium includes a 3 wt % mixture containing glucose and maltodextrin.

The nitrogen source used in the bacterial culture medium of the present example may be $(NH_4)_2SO_4$, $(NH_4)_2PO_4$, $NH_4NO_3$, $NH_4Cl$, casamino acid, urea, peptone, polypeptone, tryptone, meat extract, yeast extract, yeast powder, milk, soybean flour, whey, or any combination thereof. For example, the used culture medium includes at least one of 5 wt % to 30 wt % milk and 1 wt % to 10 wt % soybean flour.

Example 3: Analysis for Expression of Pro-Inflammatory Cytokine CXCL10

THP-1 cell is introduced herein for analyzing the ability of probiotics to modulate immunity. THP-1 cell can be differentiated into the following three macrophage types: M0 macrophage, M1 macrophage, and M2 macrophage.

THP-1 cells are seeded into a 10-cm dish at a density of $1 \times 10^6$ cells/mL, and then the cells are treated with 200 ng/mL phorbol myristate acetate (PMA) for 24 hours so that the THP-1 cells are differentiated to M0 macrophages. After cells are washed with phosphate buffered saline (PBS), the cells are treated with 5 mL trypsin, and then centrifugation at a rate of 1,500 rpm for 15 minutes is performed to obtain a cell pellet. After which, cells are seeded into a 12-well plate at $8 \times 10^5$ cells/mL, and the cells rest for 24 hours. Cells are incubated with 40 ng/mL IFN-γ and 200 ng/mL lipopolysaccharide (LPS) to be differentiated to M1 macrophages, and then the M1 macrophages are incubated for 48 hours. A probiotic sample is dissolved in a cell culture medium free of antibiotic, and then co-incubated with M1 macrophages for 48 hours (the number ratio of macrophages to bacterial strains is 1:100). After incubation, a culture medium is separated with centrifugation at a rate of 2,000 rpm for 5 minutes to obtain a supernatant. Finally, the CXCL10 amount in the supernatant is analyzed with enzyme-linked immunosorbent assay (ELISA), and the results obtained from different groups are analyzed with Ordinary one-way ANOVA assay.

As shown in FIG. 1, mixing GL-104 strain and F-1 strain at an arbitrary ratio has better activity for inhibiting the expression of pro-inflammatory cytokine CXCL10 by M1 macrophages than that of GL-104 strain alone and that of F-1 strain alone. Especially, mixing 70% F-1 strain and 30% GL-01 strain ("70% F-1+30% GL-104" group) can lead to the pronounced inhibition result.

Figure 2:
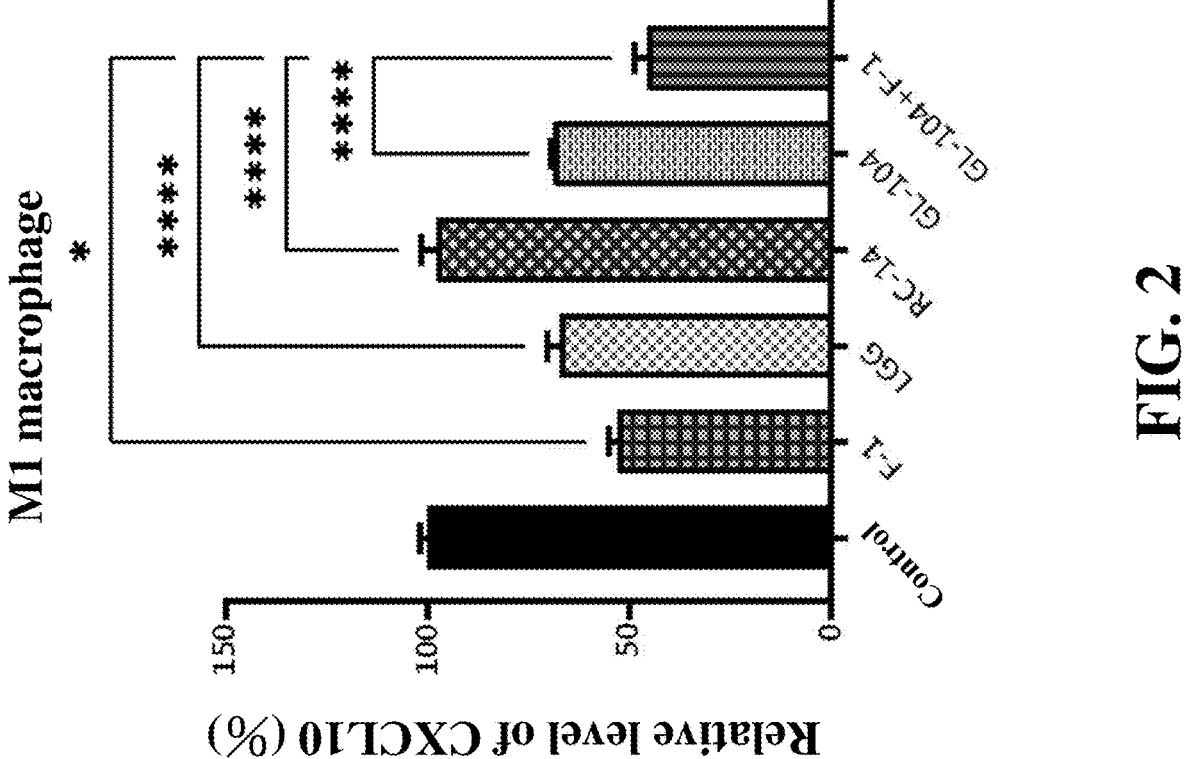
FIG. 2 is a bar graph illustrating the effect of a GL-104 strain, a F-1 strain, or other bacterial strains on pro-inflammatory cytokine CXCL10 expression by M1 macrophages, wherein * indicates $P<0.05$, and **** indicates $P<0.0001$.

As shown in FIG. 2, GL-104 strain and RC-14 strain belong to *Limosilactobacillus reuteri*, and on the condition of the same total bacterial count, GL-104 strain has better activity for inhibiting the expression of pro-inflammatory cytokine CXCL10 by M1 macrophages than RC-14 strain; F-1 strain and LGG strain belong to *Lacticaseibacillus rhamnosus*, and on the condition of the same total bacterial count, F-1 strain has better activity for inhibiting the expression of pro-inflammatory cytokine CXCL10 by M1 macrophages than LGG strain. Further, the inhibition activity of any combination of GL-104 strain and F-1 strain is better than that of GL-104 strain alone and that of F-1 strain alone.

Figure 3:
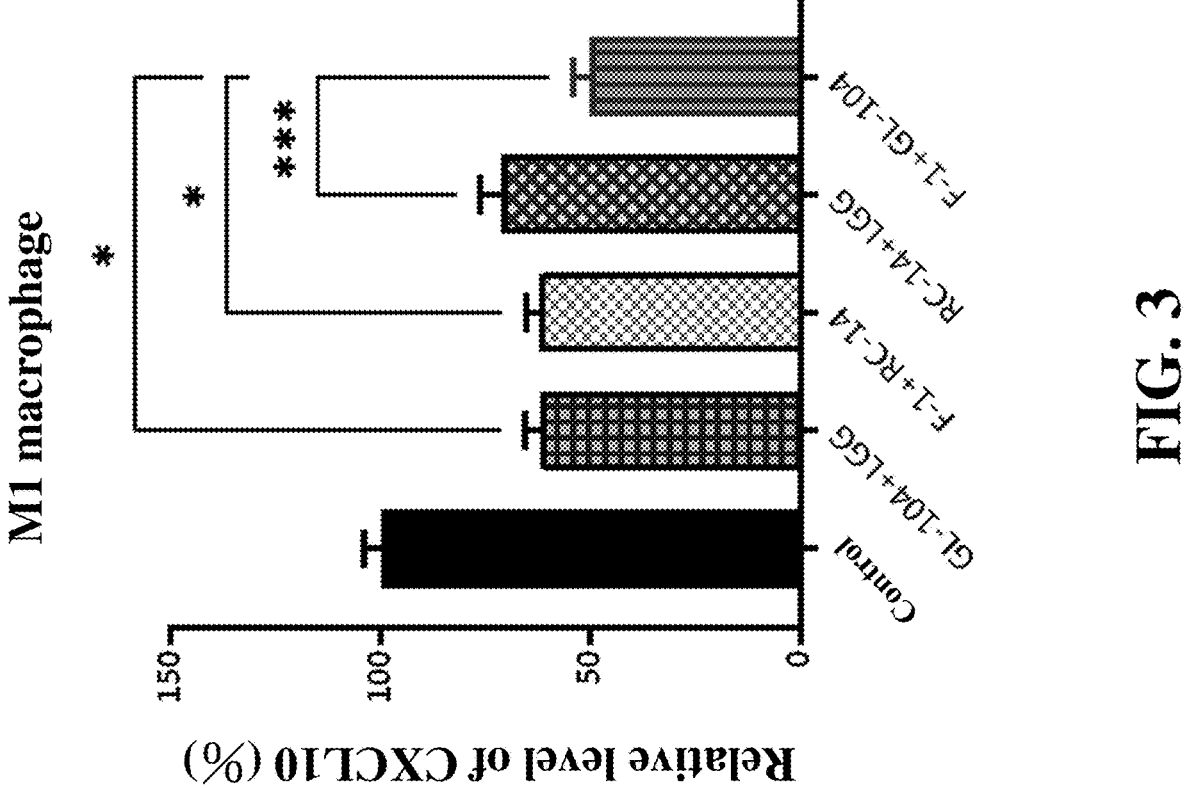
FIG. 3 is a bar graph illustrating the effect of a combination selected from two of a GL-104 strain, a F-1 strain, and other bacterial strains on pro-inflammatory cytokine CXCL10 expression by M1 macrophages, wherein * indicates $P<0.05$, and *** indicates $P<0.001$.

As shown in FIG. 3, on the condition that the bacterial counts of single strains are the same, the combination of GL-104 strain and F-1 strain has better activity for inhibiting the expression of pro-inflammatory cytokine CXCL10 by M1 macrophages than the other groups.

It is noted that the "CXCL10 relative expression level" indicated in Y axis of each figure is obtained based on the CXCL10 expression level of untreated M1 macrophages.

As above, it is proven that GL-104 strain and F-1 strain can provide synergy on M1 macrophages to inhibit the expression of pro-inflammatory cytokine CXCL10 by M1 macrophages.

Example 4: Analysis for Polarization to M2 Macrophage

THP-1 cells are seeded into a 10-cm dish at a density of $1 \times 10^6$ cells/mL, and then the cells are treated with 200 ng/mL phorbol myristate acetate (PMA) for 24 hours so that the THP-1 cells are differentiated to M0 macrophages. After cells are washed with phosphate buffered saline (PBS), the cells are treated with 5 mL trypsin, and then centrifugation at a rate of 1,500 rpm for 15 minutes is performed to obtain a cell pellet. After which, cells are seeded into a 12-well plate at $8 \times 10^5$ cells/mL, and the cells rest for 24 hours. Cells are incubated with 40 ng/mL IFN-γ and 200 ng/mL lipopolysaccharide (LPS) to be differentiated to M1 macrophages or incubated with 40 ng/mL IL-4 to be differentiated to M2 macrophages, and then the macrophages are incubated for 48 hours. A probiotic sample is dissolved in a cell culture medium free of antibiotic, and then co-incubated with M1 macrophages for 48 hours (the number ratio of macrophages to bacterial strains is 1:100). Finally, after washing cells, fluorescent staining is performed on the cells by using anti-CD206 antibody and anti-CD86 antibody as primary antibody and the corresponding antibody as secondary antibody to analyze the ratio of CD206 to CD86. Additionally, the results obtained from different groups are analyzed with Ordinary one-way ANOVA assay.

Figure 4:
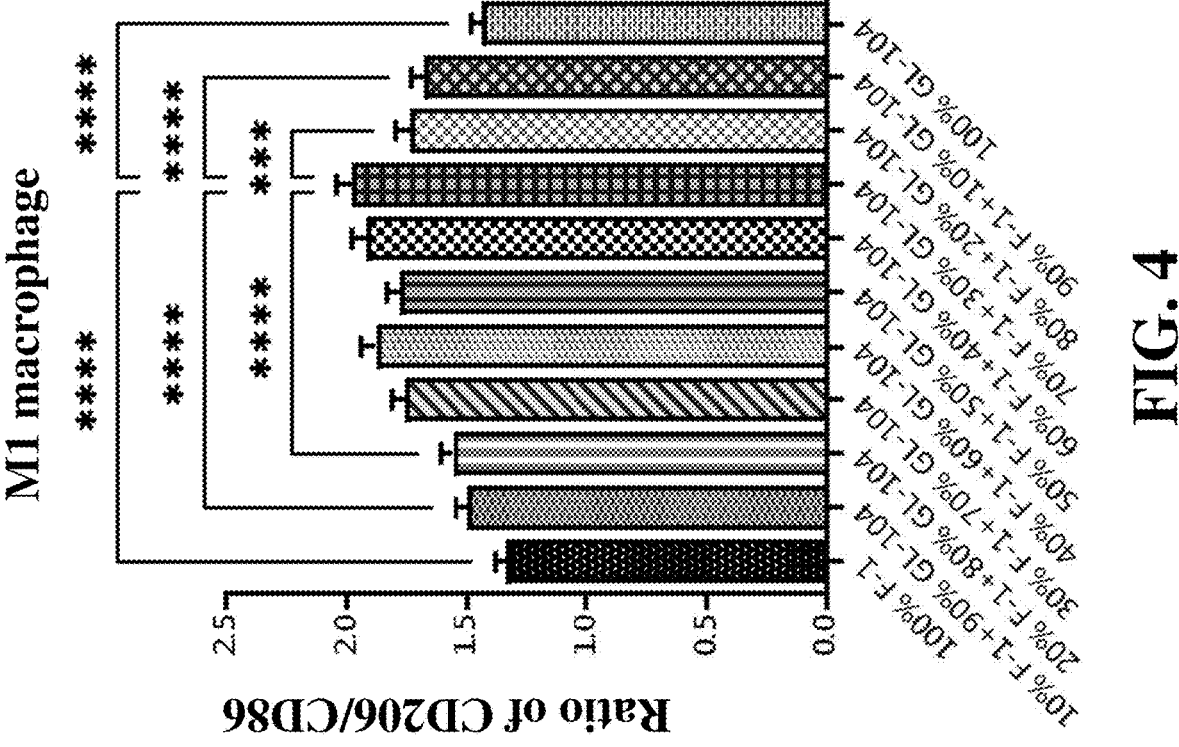
FIG. 4 is a bar graph illustrating the effect of mixing a GL-104 strain and a F-1 strain at different ratios on polarization of M1 macrophages to M2 macrophages, wherein * indicates $P<0.001$, and ** indicates $P<0.0001$.

As shown in FIG. 4, mixing GL-104 strain and F-1 strain at an arbitrary ratio has better activity for promoting polarization of M1 macrophages to M2 macrophages than that of GL-104 strain alone and that of F-1 strain alone. Especially, mixing 70% F-1 strain and 30% GL-01 strain ("70% F-1+30% GL-104" group) can lead to the pronounced promotion result.

Figure 5:
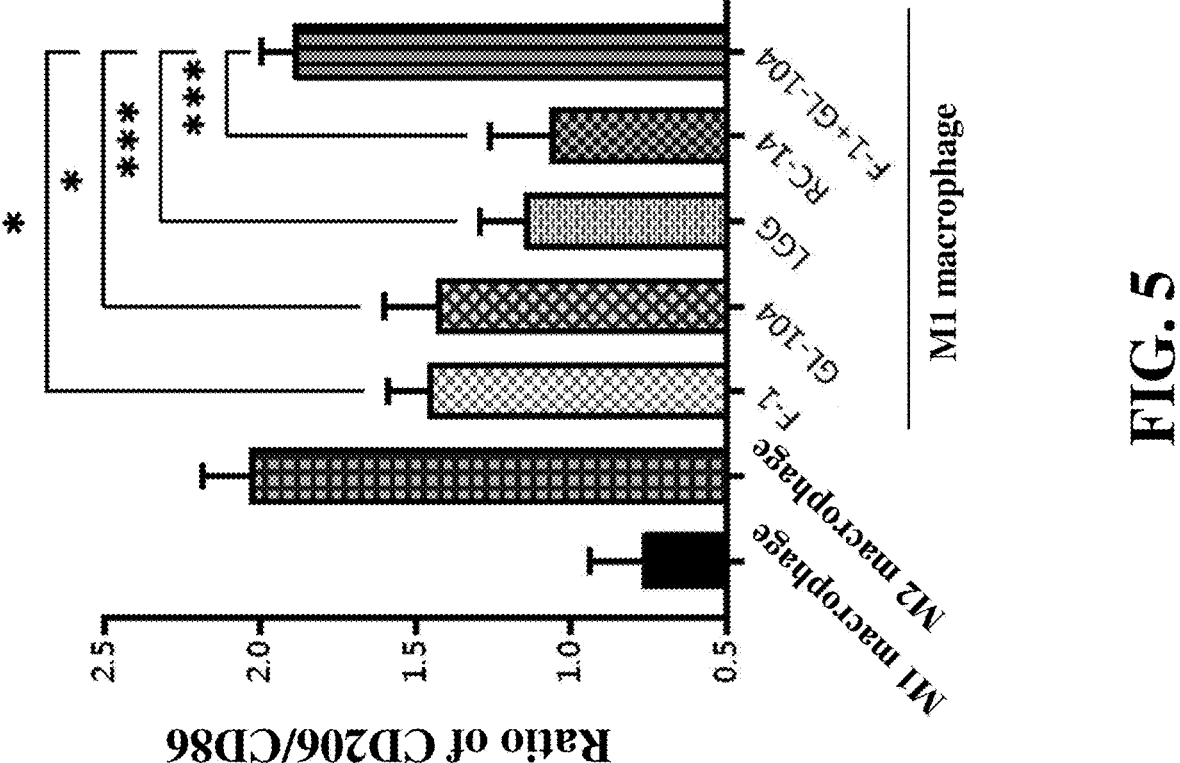
FIG. 5 is a bar graph illustrating the effect of a GL-104 strain, a F-1 strain, or other bacterial strains on polarization of M1 macrophages to M2 macrophages, wherein * indicates $P<0.05$, and *** indicates $P<0.001$.

As shown in FIG. 5, GL-104 strain and RC-14 strain belong to *Limosilactobacillus reuteri*, and on the condition of the same total bacterial count, GL-104 strain has better activity for promoting polarization of M1 macrophages to M2 macrophages than RC-14 strain; F-1 strain and LGG strain belong to *Lacticaseibacillus rhamnosus*, and on the condition of the same total bacterial count, F-1 strain has better activity for promoting polarization of M1 macrophages to M2 macrophages than LGG strain. Further, the promotion activity of any combination of GL-104 strain and F-1 strain is better than that of GL-104 strain alone and that of F-1 strain alone. Additionally, the ratio of CD206 to CD86 obtained by treating M1 macrophages with the combination of GL-104 strain and F-1 strain is close to that obtained from untreated M2 macrophages.

Figure 6:
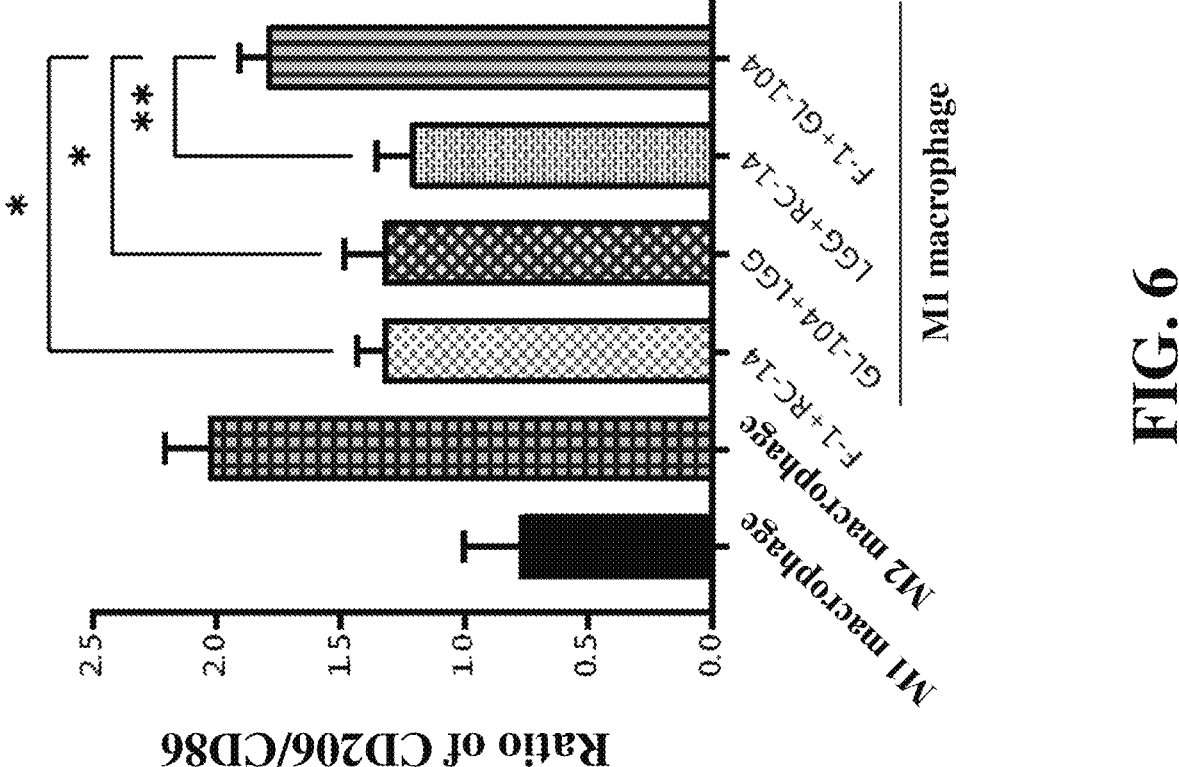
FIG. 6 is a bar graph illustrating the effect of a combination selected from two of a GL-104 strain, a F-1 strain, and other bacterial strains on polarization of M1 macrophages to M2 macrophages, wherein * indicates $P<0.05$, and ** indicates $P<0.01$.

As shown in FIG. 6, on the condition that the bacterial counts of single strains are the same, the combination of GL-104 strain and F-1 strain has better activity for promoting polarization of M1 macrophages to M2 macrophages than the other groups. Additionally, the ratio of CD206 to CD86 obtained by treating M1 macrophages with the combination of GL-104 strain and F-1 strain is close to that obtained from untreated M2 macrophages.

As above, it is proven that GL-104 strain and F-1 strain can provide synergy on M1 macrophages to promoting polarization of M1 macrophages to M2 macrophages.

While the invention has been described in connection with what is considered the most practical and preferred embodiments, it is understood that this invention is not limited to the disclosed embodiments but is intended to cover various arrangements included within the spirit and scope of the broadest interpretation so as to encompass all such modifications and equivalent arrangements.

What is claimed is:

1. A method for treating or preventing allergic rhinitis, comprising:

administering a lactic acid bacterial composition to a subject in need of reducing production of pro-inflammatory cytokine CXCL 10 by an immune cell of the subject or increasing a ratio of CD206 to CD86 on a surface of the immune cell of the subject, the composition comprising: (a) a *Limosilactobacillus reuteri* GL-104 strain; and (b) a *Lacticaseibacillus rhamnosus* F-1 strain; wherein the GL-104 strain is deposited at the China Center for Type Culture Collection with a deposition number CCTCC M209138; wherein the F-1 strain is deposited at the China Center for Type Culture Collection with a deposition number CCTCC M2011124, wherein relative to total colony forming unit of the GL-104 strain and the F-1 strain, the GL-104 strain is present at 30%, and the F-1 strain is present at 70%.

2. The method as claimed in claim 1, wherein the GL-104 strain is a viable strain or an inactivated strain, and the F-1 strain is a viable strain or an inactivated strain.

3. The method as claimed in claim 1, wherein the lactic acid bacterial composition further comprises: (c) an excipient, diluent, or carrier.

4. The method as claimed in claim 3, wherein the excipient, diluent, or carrier is a food-acceptable excipient, diluent, or carrier, or a pharmaceutical-acceptable excipient, diluent, or carrier.

5. The method as claimed in claim 1, wherein the composition is administered at a total bacterial count of the GL-104 strain and the F-1 strain from $10^6$ to $10^{10}$ CFU/kg of body weight of the subject per day.

\* \* \* \* \*